United States Patent [19]

Neudorfl et al.

[11] Patent Number: 5,859,362
[45] Date of Patent: Jan. 12, 1999

[54] TRACE VAPOR DETECTION

[75] Inventors: Pavel Slavomir Neudorfl, Ottawa; Michel Bernard Hupe, Aylmer; Gerald Drolet, Ottawa; Joseph Bernard Pierre Pilon, Perth; Andre Hanna Lawrence, Gloucester; Joseph Samuel Andre Cote, Gatineau, all of Canada

[73] Assignee: Revenue Canada, Canada

[21] Appl. No.: 734,880

[22] Filed: Oct. 22, 1996

[51] Int. Cl.[6] ................................................ G01N 7/00
[52] U.S. Cl. ........................................................ 73/23.2
[58] Field of Search ................................ 73/23.2, 863.7, 73/23.36

[56] References Cited

U.S. PATENT DOCUMENTS

| | | | |
|---|---|---|---|
| 3,883,739 | 5/1975 | Jenkins | 250/304 |
| 4,580,440 | 4/1986 | Reid et al. | 73/23 |
| 5,023,452 | 6/1991 | Purcell et al. | 250/306 |
| 5,092,156 | 3/1992 | Miskolczy | 73/1 |
| 5,142,144 | 8/1992 | Remo et al. | 250/288 |
| 5,302,191 | 4/1994 | Koutrakis et al. | 95/285 |
| 5,310,681 | 5/1994 | Rounbehler et al. | 436/106 |
| 5,350,565 | 9/1994 | Leveson et al. | 422/64 |
| 5,365,771 | 11/1994 | Gysi et al. | 73/31.03 |
| 5,394,092 | 2/1995 | Wentworth et al. | 324/464 |
| 5,395,589 | 3/1995 | Nacson | 422/88 |
| 5,405,781 | 4/1995 | Davies et al. | 436/52 |
| 5,409,839 | 4/1995 | Balestrieri et al. | 436/56 |
| 5,426,056 | 6/1995 | Nacson | 436/91 |
| 5,452,234 | 9/1995 | Heath et al. | 364/510 |
| 5,491,337 | 2/1996 | Jenkins et al. | 250/287 |
| 5,525,374 | 6/1995 | Ueda et al. | 128/719 |
| 5,528,150 | 6/1996 | Stearns et al. | 324/464 |
| 5,532,599 | 7/1996 | Stearns et al. | 324/464 |
| 5,585,575 | 12/1996 | Corrigan et al. | 73/863.71 |

FOREIGN PATENT DOCUMENTS

| | | | |
|---|---|---|---|
| 1201646 | 3/1986 | Canada | 150/6 |
| 1266621 | 3/1990 | Canada | 183/21 |
| 2015157 | 4/1990 | Canada | 73/100 |
| 2043328 | 5/1991 | Canada | G01N 30/14 |
| 2113463 | 7/1992 | Canada | G01N 027/66 |
| WO/91/09307 | 10/1990 | WIPO | G01N 30/00 |

OTHER PUBLICATIONS

Pilon, et al, Drug Vapours Sampling Methodologies: Application to Cargo Containers, Proceedings Counterdrug Law Enforcement: Applied Technology for Improved Operational Effectiveness, Part 2, (1995), Office of National Drug Control Policy, Nashua, New Hampshire.

Kim et al, Cargo Contraband Screening, (1994)Cargo Inspection Technologies, SPIE, vol. 2276, pp. 279–291.

Lawrence et al, Determination of Amphetamine, Cocaine, and Heroin Vapour Pressures Using a Dynamic Gas Chromatographic Analysis:, Canadian Journal of Chemistry, vol. 62, No. 10 (1984) pp. 1886–1888.

Brown et al, Trace Chemical Vapors in Illicit Cocaine Production and Shipping, Cargo Inspection Technologies, SPIE Proceedings, vol. 2276 (1994) pp. 340–351.

Poziomek et al, Use of chemical markers in designing detection and identification schemes for cocaine and cocaine hydrochloride, Contraband and Cargo Inspection Technology International Symposium, Proceedings, Washington, D.C., 1992, pp. 425–432.

(List continued on next page.)

Primary Examiner—Hezron E. Williams
Assistant Examiner—Jay L. Politzer
Attorney, Agent, or Firm—Leonard Bloom

[57] ABSTRACT

A method and device for the detection of vapors of cocaine and associated compounds are disclosed. The method involves sampling a volume of air suspected of containing cocaine vapors, passing this air through a filtration system that removes any particulate matter and binds vapors of cocaine and associated compounds, if present, for further analysis. A preferred associated compound-vapor is that of ecgonidine methyl ester (EDME), and a marker for the presence of cocaine. The device is comprised of a sampling, filtration and vacuum port components and can be easily attached to a container, and suction source, for the sampling of air.

17 Claims, 11 Drawing Sheets

OTHER PUBLICATIONS

Robins, et al, Analysis of Volatile Organic Compounds from Illicit Cocaine Samples, Cargo Inspection Technologies, SPIE, Proceedings, vol. 2276 (1994) pp. 352–362.

Lukaszewski, et al., Impurities and Artifacts of Illicit Cocaine, J. Forensic Sciences, vol. 25, No. 3 (1980) pp. 499–507.

Casale, et al, A Chromatographic Impurity Signature Profile Analysis for Cocaine Using Capillary Gas Chromatography, J. Forensic Sciences, vol. 36, No. 5 (1991) pp. 1312–1330.

Ensing, et al, A Rapid Gas Chromatographic Method for the Fingerprinting of Illicit Cocaine Samples, J. Forensic Sciences, vol. 37, No. 2 (1992) pp. 446–459.

Lawrence, A.H, Simple Interface for Transferring High–Boiling Compounds from Sample Adsorption Tubes onto Capillary Gas Chromatographic Columns, J. Chromatography, vol. 395 (1987) pp. 531–538.

TRACE VAPOR DETECTION

The present invention relates to a method and an apparatus for detection of cocaine and its related compounds as vapours. More specifically this invention is directed to the detection of these vapours within an enclosed space such as baggage, parcels, cars, trucks and cargo containers.

BACKGROUND OF THE INVENTION

Full citations of the references appear after the Examples section.

Through careful inspection, intelligence, undercover operation and surveillance, customs and police officers worldwide manage to interdict tons of illicit drugs per year. However, because they are overwhelmingly outnumbered by their adversary, the quantity of seized drugs represents only a fraction of the total volume of the drugs trafficked. The use of large marine containers is a well known smuggling method for large shipments of drugs. Such containers present an ideal method of smuggling as the examination method is time consuming for Customs personnel and costly to the importing community. For these reasons, the interdiction of drugs through marine containers is a high priority item for Customs officials in the U.S., Canada and Western Europe.

To date, the most reliable method for searching containers involves manual unloading of the cargo (de-stuffing) and careful screening of each item by manual inspection. Because of limited resources, relatively few containers can be examined in this manner. Thus, a detection aid allowing rapid pre-screening of the containers is required to distinguish between innocent and suspicious cargo. The fundamental objective of providing technical support to the law enforcement officer is to improve this situation.

In the past, the only known detection aid used in customs work throughout many countries to search out narcotics was the so-called 'drugs' dog. Appropriately trained dogs can be an effective means of rapidly examining large quantities of baggage and freight in spite of several drawbacks. A dog can only work for a certain length of time and its enthusiasm and interest can vary.

Accordingly, there has been interest and steady growth in research and development in the field of instruments for the detection of illicit drugs.

Instrumental methods of detecting concealed drugs may be categorized under two main headings, bulk detection techniques and chemical sensing techniques. In bulk detection techniques, suspect items to be examined are subjected to electromagnetic or ionizing radiation and the presence of drugs is determined by the interaction of the bulk content of the item with the probing field. These include X-ray imaging, gamma backscatterring and thermal neutron activation. For example, X-ray examination of loaded cargo containers is being used. However this technique requires very large and expensive facilities; furthermore, X-ray systems provide little in the way of a specific and distinguishing signal for narcotics.

Chemical sensing techniques are based on the chemical analysis of air or wipe samples obtained from within, from the exterior surface or from the vicinity of a suspect item, to determine trace amounts of drugs and/or drug-related constituents. These constituents may be present in the form of vapours or microscopic particles. All chemistry based drug detectors are composed of two parts: a sampler and an analyzer.

The function of the sampler is to collect the drugs, as vapours or particulates, on a filter which is then brought to the inlet of the analyzer where it is heated and analyzed. The analyzers use principles such as ion mobility spectrometry, gas chromatography and mass spectrometry. The sampling strategy and methodology is fundamentally different for preconcentration of vapours and the collection of solids, either airborne or bound to surfaces. This must be taken into account when collecting samples to determine the presence of smuggled cocaine.

Drug detection methods have been developed which rely on the presence of particulates (5–100 microns) for detection of drugs of interest (U.S. Pat. No. 4,580,440, and/or U.S. application No. 08/352,486 U.S. Pat. No. 5,576,976, both of which are incorporated by reference). This method has been used with some success at airports, penitentiaries, land border crossings for small vehicles, at marine ports for boat searches, and at postal plants. When applied to cargo containers, however, the sampling of particulates has limitations:

Particulates may not be present if the cocaine has been packaged carefully.

For effective sampling, the sampling device must come in direct contact with the cocaine particle; this makes particle sampling very site specific within the cargo container.

Particulates can remain in a container for a long period of time and generate alarms in containers previously used for smuggling but no longer holding the contraband.

Cross contamination between the contents of a container can lead to alarms in the wrong area of the container.

Previous work on the vapour pressure of cocaine base [1] showed that, at room temperature, a saturated headspace of cocaine contains approximately 3 ng of cocaine vapors per litre of air. In cargo shipments, however, it is unlikely that conditions will exist to allow the presence of a saturated vapor pressure of cocaine because the smuggled drug consists mainly of cocaine hydrochloride whose vapor pressure is lower than that of cocaine base. Furthermore, the salt of cocaine is normally enclosed in a wrapping material which would hinder the escape of vapors.

A system for the detection of organic vapors in air that are then adsorbed onto a film of fullerenes on a metallic substrate, and released for their detection is disclosed in U.S. Pat. No. 5,395,589 (Inventor: Nacson S; issued Mar. 7, 1995). In U.S. Pat. No. 5,426,056 (issued Mar. 8, 1995) Nacson also discloses a detector for analyzing ionized organic molecule vapors within a sample. The detection of residues from samples by gas chromatography is disclosed in U.S. Pat. No. 5,142,144 (inventor Remo J L, and Turner R.; issued Aug. 25, 1992).

The collection of vapors of nitrogen-containing compounds involving a plurality of open-ended small diameter tubes coated with silicone to trap these vapors and release the vapor upon heating for subsequent detection by gas chromatography is taught in U.S. Pat. No. 5,092,156 (inventor Miskolczy G; issued Mar. 3, 1992).

Although illicit cocaine samples have been shown to emit other vapors such as acetone (a product associated with the manufacture of cocaine), methyl benzoate, benzoic acid (both are decomposition products of cocaine, see (9)) and lidocaine (a cutting agent), such vapors may also be emitted by other licit products, and if the screening processes were based on the detection of these vapors, this might result in high false alarm rates (U.S. Pat. No. 4,580,440).

Ideally, the detection of cocaine would be verified by detecting another compound that is associated with cocaine, but one that is not typically found in association with other chemicals. Furthermore, the associated compound would have a similar or greater volatility (vapor pressure) to cocaine. The ideal cocaine-related compound would also dissipate readily from within a container so that the co-detection of cocaine along with this related compound would ensure the occurrence of cocaine within the container.

The inventors have discovered that many cocaine seized samples not only emit relatively small amounts of cocaine vapors but, more importantly, emit vapors of ecgonidine methyl ester (EDME), a well known structurally related degradation product of cocaine comprised of a bicyclic skeleton. Although EDME has been observed previously in GC-MS analyses of solutions of seized cocaine samples [5,6], it has never been reported in the vapor phase. We have observed that the vapor pressure of EDME is larger than that of cocaine by 5 orders of magnitude (23000 ppb vs 0.25 ppb) at room temperature. Therefore, the high vapor pressure of EDME makes it a likely candidate for detection by trapping vapors from a cargo container. Due to the increased vapor pressure of EDME, this chemical disappears more rapidly than the vapors associated with cocaine from within a container. Therefore, the detection of both cocaine and EDME vapors provide a reliable indicator, by reducing the number of false positives, of the presence of cocaine within the sampled container.

SUMMARY OF THE INVENTION

The present invention relates to a method and device for the detection of vapors of cocaine and associated compounds in air.

According to the present invention there is provided a method for the detection of vapors of cocaine and associated compounds, comprising obtaining a sample of air, passing the sample through a filter capable of retaining the vapors of cocaine and associated compounds, and detecting the presence of cocaine and associated compounds from the filter, wherein the associated compounds exhibit the property of having a volatility that is different from that of cocaine. Preferably, vapors of the associated compounds include those that exhibit the property of having a higher vapor pressure than that of cocaine, such that if the occurrence of the vapors of EDME, or vapors of cocaine and the associated compound are co-detected, then this is an indication of the presence of cocaine in the contained space. More preferably, the vapor of the associated compound is that of ecgonidine methyl ester.

This invention also provides for a method for the detection of vapors of cocaine and associated compounds wherein the filter, capable of retaining vapors of cocaine and associated compounds, is made up of any suitable matrix such as, but not limited to, tissue cloth or mesh made from cotton, silanized glass wool, metal or TEFLON®. Also embraced by this invention are filter materials comprised of a suitable matrix that are coated with a substance, which remains on the filter, to enhance the binding of vapors of cocaine and associated compounds. It is preferred that at least one of the filters is a coated TEFLON® filter. Furthermore, it is preferred that the substance to enhance the binding of vapors of cocaine and associated compounds is a dilute acid solution. Examples of suitable dilute acid solutions include, but are not limited to, citric acid, oxalic acid, phosphoric acid and the like. Preferably, the acid is a dilute solution of citric acid for example a 1% citric acid solution in methanol, or acetone or any low-boiling alcohol or ketone.

This invention also relates to the above method wherein any vapors trapped on the coated filter are released by the action of heat in the presence of an alkaline medium, such as an alkali metal or alkali earth metal oxides and hydroxides and preferably soda lime (calcium oxide and sodium hydroxide), and the released compounds are detected using ion mobility spectrometry (IMS), IMS-mass spectrometry (MS), gas-chromatography (GC), GC-MS, or GC-MS-MS.

This invention also provides for a device for sampling air containing vapors of cocaine and associated compounds, comprising a nozzle made up of:

a) a sampling component comprising a surface circumscribing an opening for the passage of air, and b) a filtering component comprising a filtration device and vacuum port, such that the filtration device is placed in the path of air obtained from the sampling component as it is withdrawn through the vacuum port, said filtration device comprised of a plurality of filters, capable of removing particulates from the air, at least one of which is capable of binding vapors of cocaine and associated compounds.

This invention also provides for device as described above, wherein the plurality of filters comprises at least one TEFLON® filter. Furthermore, this filter can be coated with a substance to enhance binding of the cocaine and its related vapors. An example of one such substance for coating the filter includes, but is not limited to, a dilute acid solution, for example a citric acid.

This invention also embraces a filter capable of binding vapors of ecgonidine methyl ester. Preferably the filter is coated with a substance to enhance the binding of ecgonidine methyl ester, for example citric acid.

Although the present invention is exemplified by the detection of vapors of cocaine and ecgonidine methyl ester, in practice any vapor of cocaine-associated compounds can be detected using the method and device of this invention.

BRIEF DESCRIPTION OF THE DRAWINGS

These and other features of the invention will become more apparent from the following description in which reference is made to the appended drawings wherein:

FIG. 3 provides several examples of vent-types found on cargo containers.

FIG. 7 is an Ion Mobility Spectrometer profile of a sample obtained from the apparatus of FIG. 6. Cocaine is identified as "1011", EDME ("seizure") as "102" nicotinamide 100.

FIG. 8 shows the identification of EDME from a seized sample.

DESCRIPTION OF PREFERRED EMBODIMENT

The present invention is directed to sampling vapors as an indication of the presence of cocaine and related compounds as vapours within a container, particularly cargo containers. Vapors which may be present in cocaine are listed below:

Volatile solvents. These are used in the extraction and purification steps of cocaine manufacture [2,3]. These solvents may not be present in all seized cocaine samples; furthermore, their presence in a container is not specific to the presence of cocaine.

Cocaine base. Cocaine base has a measurable vapor pressure [1] and the presence of cocaine vapours in the headspace of seized cocaine samples has been cited [4].

Impurities and/or decomposition products which are structurally related to cocaine and which may be present from the extraction and/or preparation of cocaine [5,6,7]. These are of high interest since their presence in a vapor sample would give a strong indication of the presence of smuggled cocaine. These impurities and/or decomposition products which are structurally related to cocaine are referred to herein as "associated compounds".

By "coated TEFLON®" it is meant a filter material comprised of Teflon® that has been treated with a dilute solution of acid. Examples of such dilute solutions include citric acid, oxalic acid, and phosphoric acid (see Example 4). However, it is to be understood that the use of TEFLON® is merely exemplary as it is only one of many suitable filter substrates that could be coated with a dilute acid solution for the purposes of trapping compounds for further analysis.

By "Gerry bag" it is meant a "cotton filter" (U.S. patent application No. 08/352,486 U.S. Pat. 5,571,976, which is incorporated by reference.), and the two terms should be used interchangeably.

The inventors have discovered that many cocaine seized samples not only emit relatively small amounts of cocaine vapors but, more importantly, emit vapours of EDME a well known degradation product of cocaine. Although EDME has been observed previously in GC-MS analyses of solutions of seized cocaine samples [5,6], it has never been reported in the vapor phase.

The inventors have discovered that this chemical permeates readily through polyethylene, does not adsorb on surfaces as readily as cocaine, and its vapor pressure at room temperature (of approx. 23,000 ppb) is 5 orders of magnitude higher than cocaine which makes it a likely candidate for detection by air sampling and a good marker for the detection of cocaine in closed containers. Due to the high vapor pressure of EDME, upon the removal of cocaine from a contained space, the vapor of EDME disappears more rapidly than those of cocaine and it is therefore a good marker for the detection of cocaine within a container.

Figure 1:
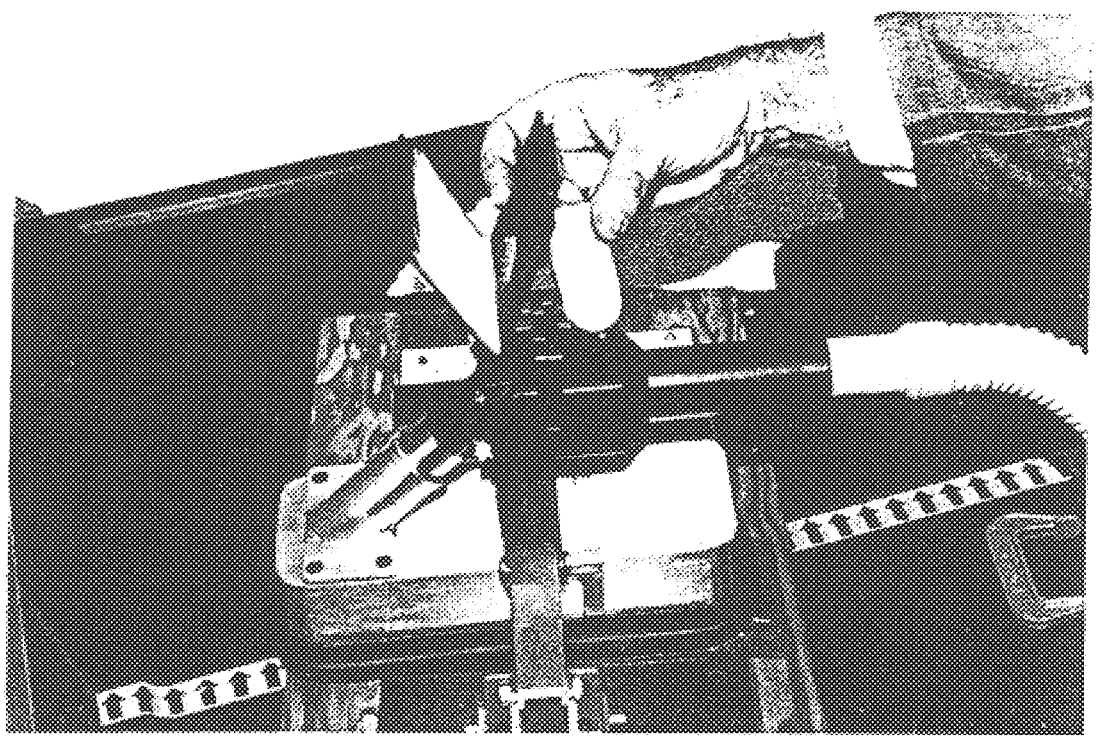
FIG. 1 is a view of the sampling head which consists of a filter assembly attached to an aluminum sampling nozzle. The filter assembly is detachable and located between the aluminum head and a vacuum hose fitting. This assembly can be rotated around the aluminum sampling nozzle. The assembly is fitted with a rubber skirt to provide a seal around the container vent and magnetic holders that attach the aluminum head assembly and support accompanying vacuum hoses. The magnetic holders ensure a good seal between the assembly and container vent. During use the vacuum hose is fitted to suction pump.
Figure 2:
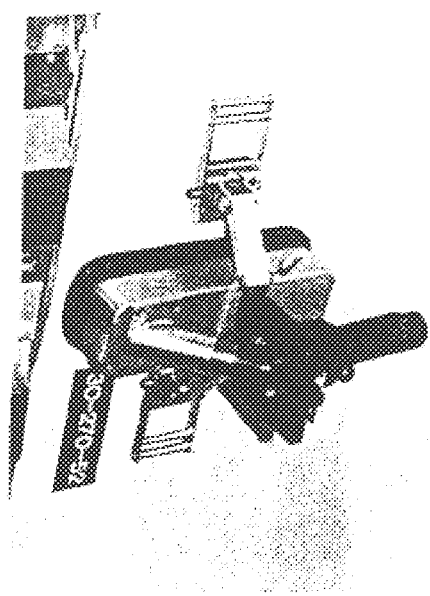
FIG. 2 is a detail of the aluminum sampling nozzle showing the magnetic holders extending from either side of the nozzle.

It has been discovered that cocaine and especially EDME vapors emitted from illicit cocaine samples concealed in suspect items and more specifically in cargo containers can be collected on specially treated TEFLON® filters, using either low or high volume suction pumps which can sample air at flows of up to approximately 200 L/min. These filters are protected from airborne dust and solid particulates by pre-filters. Although both the treated filters and pre-filters are optimized for the collection of cocaine-related compounds as vapours such as, but not limited to, EDME, the filters are also capable of trapping cocaine vapors if present in the air. The filters are enclosed in a special assembly attached onto the vacuum hose which in turn is attached to the suction pumps. The sampling nozzle with a filter assembly is illustrated in FIGS. 1 and 2.

Figure 3A:
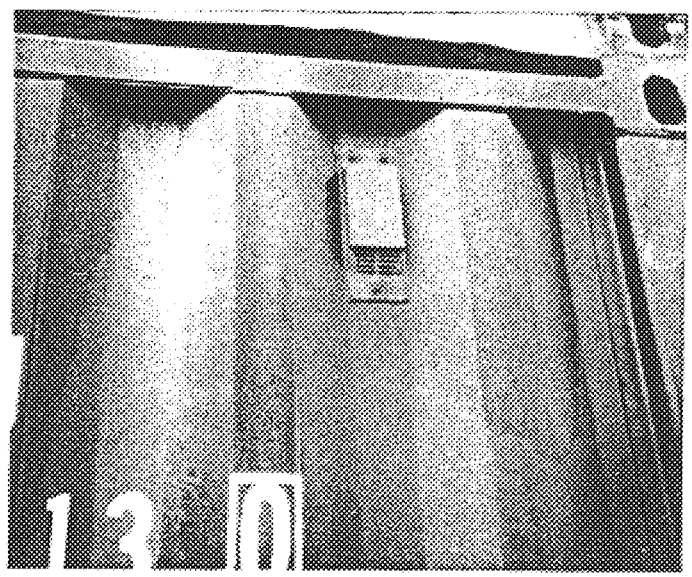
FIG. 3(A) shows typical vents found on cargo containers in Canadian and U.S. ports.
Figure 3B:
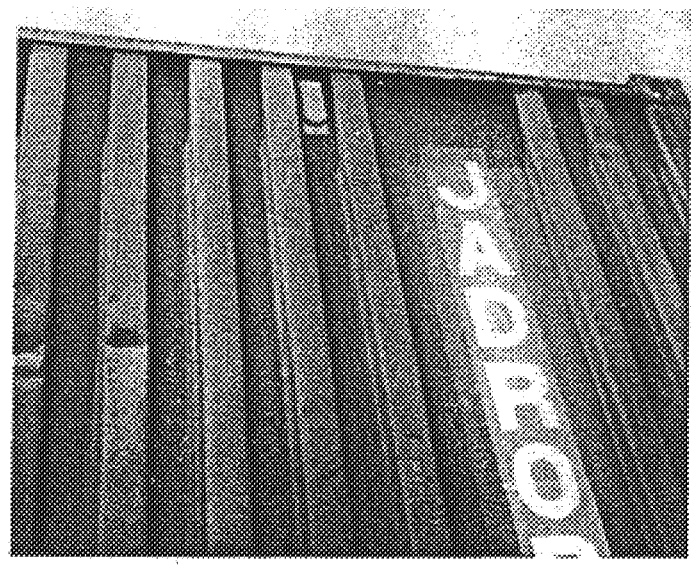
FIG. 3(B) shows another vent type.
Figure 4:
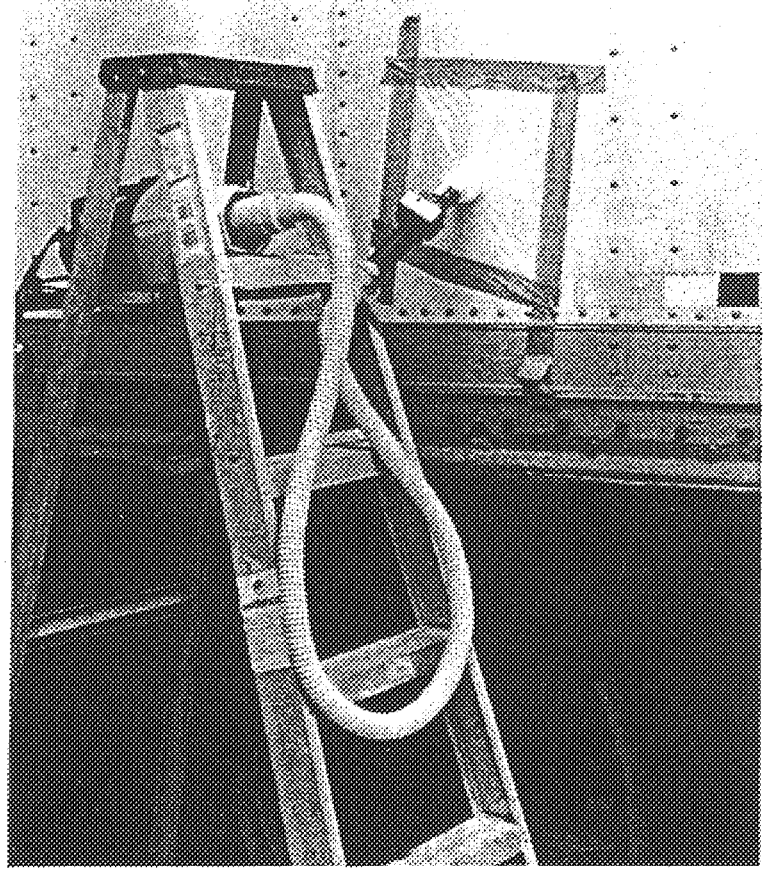
FIG. 4 shows a method for the sampling of air within a cargo container that otherwise lacks any vents. After a hole is drilled into the container a sampling nozzle is attached and sealed over the drilled hole.

For the sampling of containers, sampling nozzles, made of plastic or metal, are used to connect the filter assembly to the side ventilation ducts normally present on the side of containers, allowing to sample the inside air without opening the doors of the containers. FIGS. 3(A) and 3(B) depict vents typically encountered when sampling the containers. Furthermore, in order to minimize the collection of unwanted particulates, the container should not be agitated. Some containers do not have any vents. In those containers, holes are drilled in the walls to allow the withdrawal of inside air. The sampling nozzles can be attached to the container walls using duct tape or magnets. FIG. 4 shows the sampling of such a container.

The air sampling method as described in the present invention provides an effective pre-screening method for the detection of cocaine concealed in cargo containers. Air can be withdrawn from the inside of the container and analyzed by IMS, GC/MS or other analytical technique that are known to one of skill in the art for traces of telltale vapours uniquely associated with the drug. This method allows screening of the containers without de-stuffing, opening the doors, or even breaking the seals, because the air is conveniently withdrawn from side ventilation ducts of the containers.

Based on the present data, a correlation exists between the presence of EDME vapours and the presence of large amounts of cocaine in a container. Since EDME is more volatile than cocaine (see above), it will disappear shortly after the quantity of the drug is removed.

EXAMPLES

Instrumentation:
Ion Mobility Spectrometer

The Ion Mobility Spectrometer (IMS) used was an Ionscan 400 from Barringer Research Limited, using the parameters outlined in Table 1.

TABLE 1

| Ionscan Operating Parameters | |
|---|---|
| Drift Tube Temperature: | 238° C. |
| Inlet Temperature: | 280° C. |

TABLE 1-continued

Ionscan Operating Parameters

| | |
|---|---|
| Desorber Temperature: | 290° C. |
| High Voltage: | 1800 V |
| Drift Tube Length: | 6 cm |
| Drift Gas Flow: | 300 cc/min |
| Sample Gas Flow: | 200 cc/min |
| Analysis Time: | 20 seconds |
| Calibrant: | Nicotinamide |
| Scan period: | 20 msec |

Ion Mobility Spectrometer—Mass Spectrometer

The instrument consists of a PCP IMS instrument coupled to an EXTREL quadrupole mass spectrometer, using the parameters outlined in Table 2.

TABLE 2

IMS-MS Operating Parameters

| | |
|---|---|
| Inlet Temperature: | 235° C. |
| Cell Temperature: | 235° C. |
| Flange Temperature: | 240° C. |
| Voltage: | 250 V/cm |
| Length of Drift Cell: | 5 cm |
| Scan period: | 20 msec |
| Gate Period: | 200 μsec |
| MS Parameters, Full Scan Mode | |
| Number of scans: | 256 |
| Sweep rate: | 1000 amu/sec |
| Dwell time: | 300 μsec |
| Mass Range: | 100 to 407 amu |
| IMS Gate Open | |
| High Voltage to Electron Multiplier: | 2500 V |
| MS Parameters, Single Ion Mode | |
| Mass selected: | 181 amu, 199 amu. |

Gas Chromatograph—Mass Spectrometer

The GC-MS is a Varian Star 3400 CX GC Series, equipped with a Saturn 3 (Iontrap) detector, operated under the conditions shown in Table 3.

TABLE 3

GC/MS Conditions

Column: 25 m DB-5 MS
0.25 mm internal diameter
0.25 μm film thickness
Helium carrier gas, flow rate 1.0 mL/min
Conditions:

Oven Initial Temperature: 50° C.,
Initial hold 1.0 min.
Temperature program rate 25° C./min, final temperature 300° C.
Final hold time: 4.0 minutes
Injector temperature: 250° C.
Transfer line temperature: 290° C.
1 μL injection
Splitless mode
Mass Spectrometry Trap temperature 280° C.
All mass spectra acquired in electron impact mode, 70 eV
Mass range 65 to 350 amu
Scan rate 1.0 scan/sec
Autotune parameters were used.

Gas Chromatograph—Mass Spectrometer—Mass Spectrometer

The GC-MS-MS is a Varian Star 3400 CX GC Series, equipped with a Saturn 3 (Iontrap) detector, operated under the conditions shown in Table 4.

TABLE 4

Varian 3400CX Gas Chromatograph / Saturn 3 System Parameters

GC Conditions injector temperature 275° C.
initial oven temperature 50° C.
initial temp. hold time 3.0 min
ramp 25° C./min
final temperature 300° C.
hold time 7 min (total run time 20.0 minutes)
transfer line 295° C.
splitless injection for 3 minutes
Column DB-5MS, 30 meters, 0.25 mm I.D., 0.25 μm film thickness
carrier gas Helium at constant flow, 1.0 ml/min
Mass spectrometer (Ion Trap) parameters trap temperature 280° C.
trap operated in ms/ms mode as follow:
mass 152 isolated and dissociated for EDME (m/z 78, 80 and 94 integrated)
mass 182 isolated and dissociated for Cocaine (m/z 82, 122 and 150 integrated)

Example 1

Permeability of Cocaine base and Cocaine Hydrochloride through Polyethylene.

Figure 6:
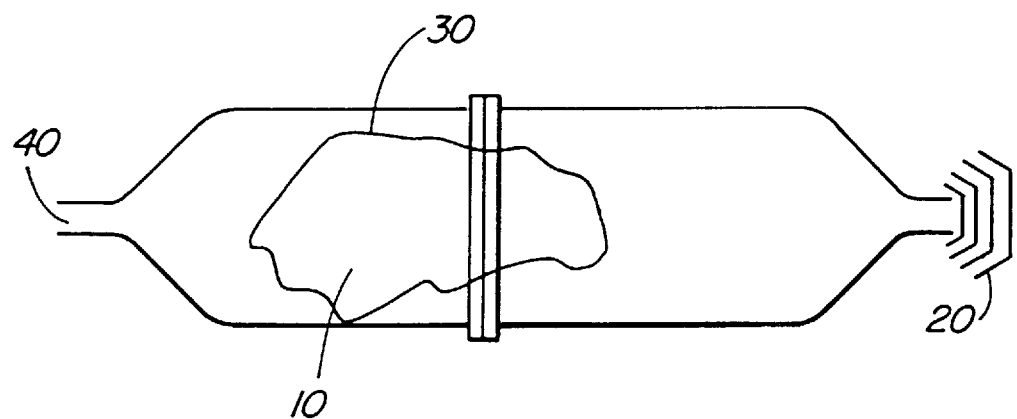
FIG. 6 is a schematic of the apparatus used to determine the passage of cocaine and related vapors from within a seized sample in a polyethylene bag. Shown are the multi layers of tissue used for the sample collection.

Smuggled cocaine consists mainly of cocaine hydrochloride which is normally enclosed in wrapping material. As a first step in the experimentation, we investigated the permeability of various cocaine and cocaine hydrochloride samples through a single layer of polyethylene (PE). The apparatus used for the study is shown in FIG. 6. Cocaine base 1 from Sigma Chemicals and a sample of cocaine hydrochloride were placed within single layer of PE 30 (thickness, 50 μm). A piece of tissue paper (20) was placed on the underside of the polyethylene. The tissue paper was removed after a residence of 16 hours for cocaine base and one hour and fifteen minutes for cocaine hydrochloride and analyzed directly by IMS (operating parameters, Table 1).

In both cases, a large cocaine peak was observed (see FIG. 6(B)). Repeating the experiment for shorter periods of time indicated that a measurable amount of cocaine was collected onto the tissue paper in less than 30 minutes.

Example 2

Transport Properties of Cocaine.

Figure 5A:
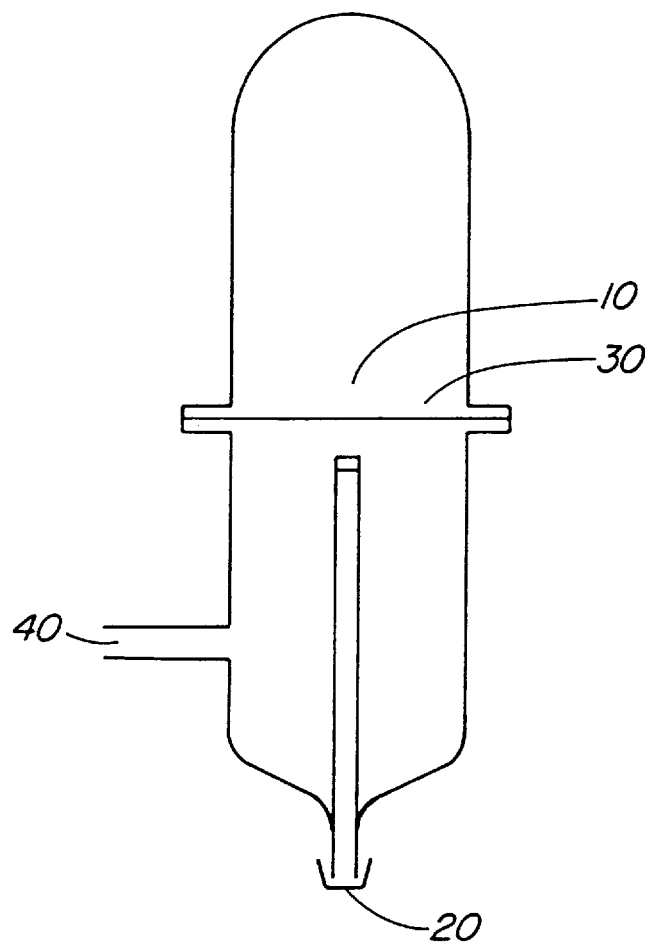
FIG. 5(A) is a schematic of the apparatus used to determine the passage of cocaine and related vapors through polyethylene.
Figure 5B:
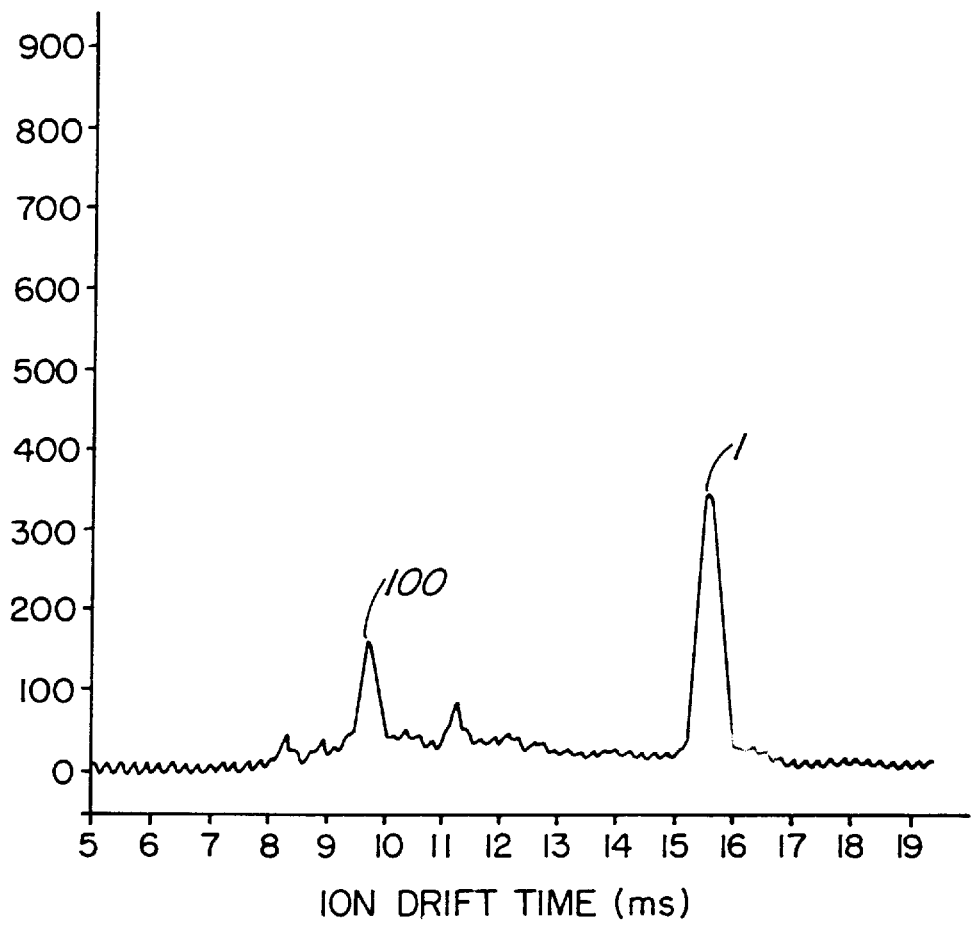
FIG. 5(B) is an Ion Mobility Spectrometer profile of a sample obtained from the apparatus of FIG. 5(A) indicating the presence of cocaine at "1, nicotinamide at 100".

Using the apparatus in FIG. 5A, and cocaine base (10), the tissue paper underneath the polyethylene was (30) removed and dry air (40) (flow of 30 to 50 cc/min) was allowed to pass along the underside of the polyethylene sheet. The vapors were collected on a tissue paper at the exit tube.

Air was passed for 192 hours before a cocaine peak was observed by IMS from the tissue paper, indicating that the cocaine vapors get adsorbed on the glass tubing as it flows towards the tissue paper.

In addition, we proceeded to investigate seized samples of cocaine to determine whether cocaine vapors are also emitted from such samples. Three seized cocaine samples (80 to 97% pure) were obtained from Health and Welfare Canada (HWC). All particles were removed from the outside of the polyethylene bag in which the samples were stored by thorough washing of the surfaces in warm water. The bag was considered clean when a tissue paper used to wipe the outside of the bag did not generate an alarm for cocaine on the IMS. The bag was placed in the apparatus shown in FIG. 6 and dry air (flow of 50 cc/min) was passed over the bag.

The vapors were collected on four consecutive layers of tissue paper. The tissue paper was analyzed by IMS at different time intervals. The results shown in Table 5 indicate that cocaine vapors permeated through a single layer of polyethylene, along with the vapors from ecgonidine methyl ester (EDME). The identification of EDME is described in Example 3.

Figure 7A:
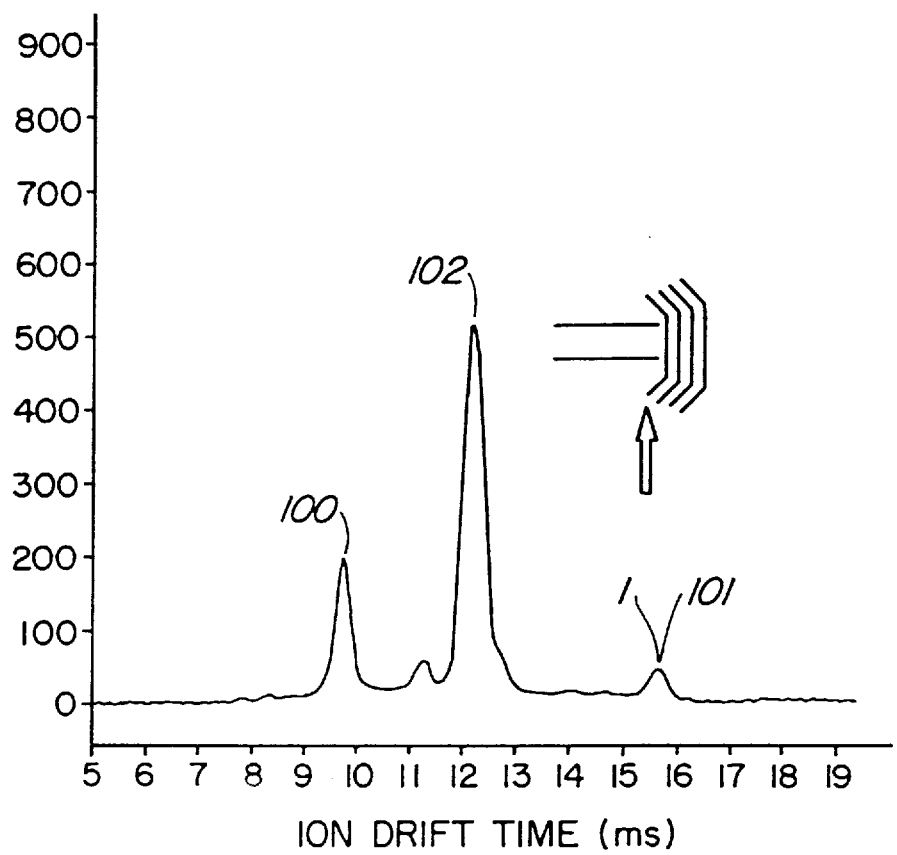
FIG. 7(A) is the profile obtained from the inner most tissue from the apparatus of FIG. 6 following sample treatment.
Figure 7B:
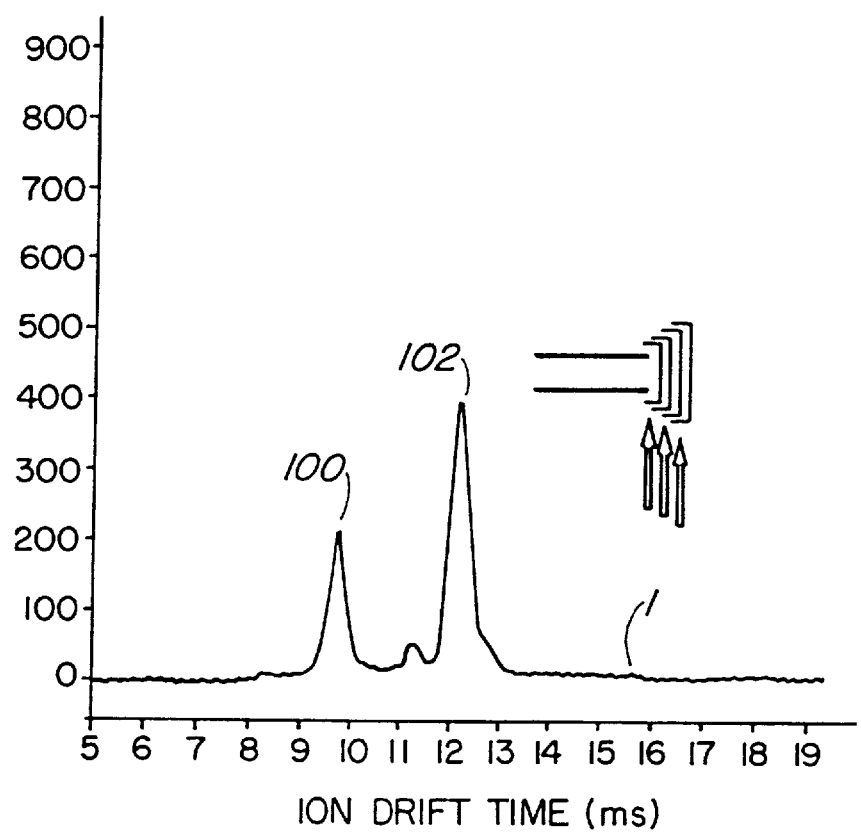
FIG. 7(B) is the profile obtained from the remaining three outer tissues of the apparatus of FIG. 6, following sample treatment.

The results also indicate that cocaine adsorbs readily on tissue paper, as evidenced by the presence of a cocaine peak in the analysis of the innermost filter only (FIG. 7(A)). The subsequent filters show only EDME (FIG. 7(B)). Thus, EDME is not as readily adsorbed as cocaine on untreated surfaces.

TABLE 5

Results of Analysis of Tissue Papers by IMS

| Time (hours) | Tissue Paper Number | Cocaine | EDME |
|---|---|---|---|
| 0–72 (72) | 1 | Yes | Yes |
| 72–95 (23) | 1 | Yes | Yes |
|  | 2 | No | Yes |
|  | 3 | No | Yes |
|  | 4 | No | Yes |
| 95–118 (23) | 1 | Yes | Yes |
|  | 2 | No | Yes |
|  | 3 | No | Yes |
|  | 4 | No | Yes |
| 118–140 (23) | 1 | Yes | Yes |
|  | 2 | No | Yes |
|  | 3 | No | Yes |
|  | 4 | No | Yes |
| 140–163 (23) | 1 | Yes | Yes |
|  | 2 | No | Yes |
|  | 3 | No | Yes |
|  | 4 | No | Yes |

Example 3
Identification of Ecgonidine Methyl Ester

The identity of ecgonidine methyl ester (EDME) was established using an IMS-MS instrument (operating parameters, Table 2). The experiment consisted of three parts:

1) the determination of drift times in the IMS for the substances of interest;

2) the determination of masses in a full ion/mass mode, using the IMS as an ionization source for the MS;

3) the determination of the mass(es) causing a peak at a certain drift time, using the MS in single ion monitoring mode as a detector for the ion mobility spectrometer.

Figure 8A:
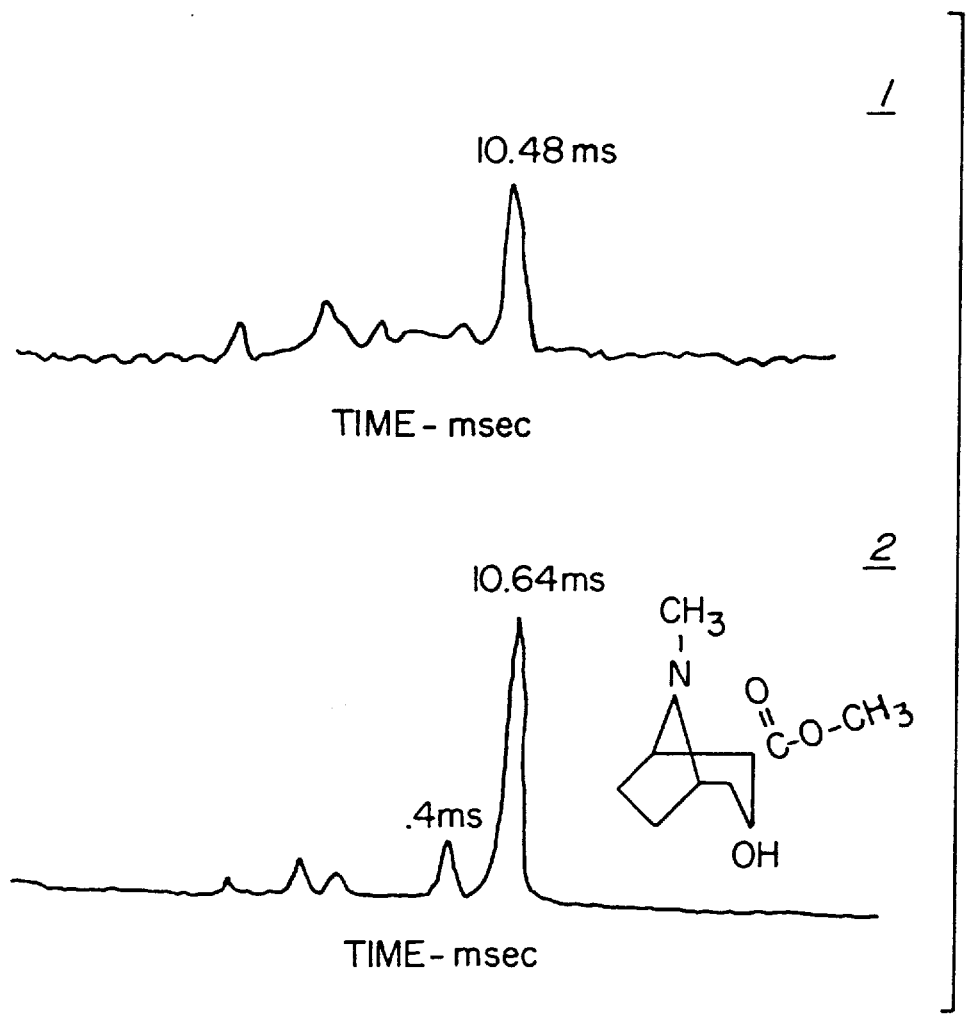
In FIG. 8(A) the IMS profile of the seizure sample 1 is displayed along with a profile of ecgonine methyl ester 2.
Figure 8B:
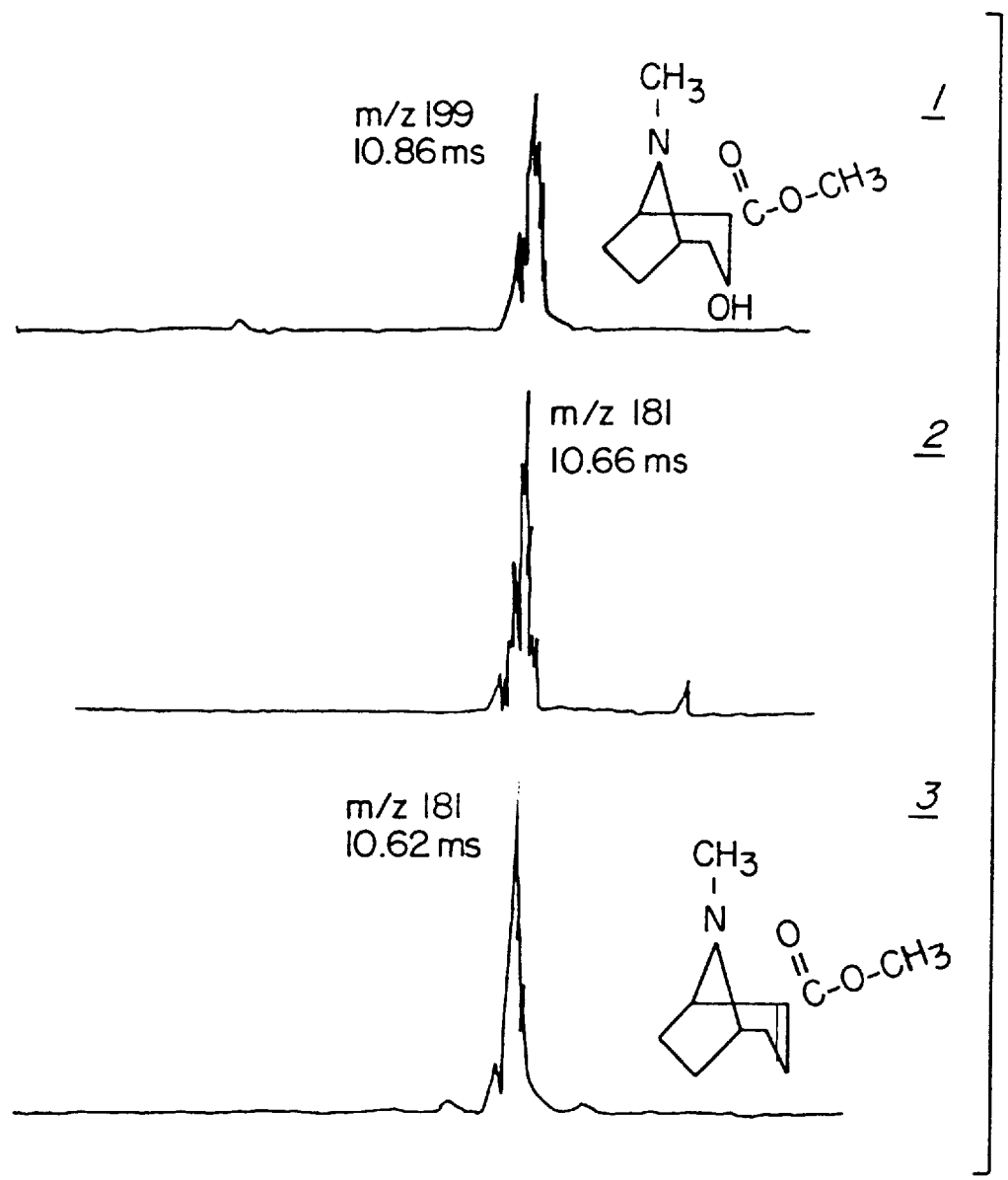
FIG. 8(B) shows the IMS-MS spectra of ecgonine methyl ester 1 (m/z 199, 10.86 ms), a degradation product of ecgonine methyl ester 2 (m/z 181, 10,66 ms) identified to be EDME 3, and an unknown compound in a seized sample which has been identified as EDME (m/z 181, 10,62 ms).

The IMS spectrum of the decomposition product from the cocaine seized samples shows a peak at 10.48 msec while ecgonine methyl ester shows a peak at 10.64 msec (see FIG. 8(A)). The IMS-MS spectrum of ecgonine methyl ester (FIG. 8(B)) indicates that the peak at 10.64 msec is caused by ions of masses 181 and 199. The peak at 10.48 msec of the decomposition product is caused by mass 181 only (FIG. 8(B). This peak was also observed from a GC-MS analysis of the vapor and is assigned to ecgonidine methyl ester (EDME). EDME has been observed previously in GC-MS analyses of solutions of seized cocaine samples [5,6]

Example 4
Determination of Vapor Pressure of EDME

For trapping cocaine vapors, silanized glass wool or cotton may be used. Effective materials for the adsorption of EDME were determined by placing a small tube filled with various materials at the output of an EDME vapor source, at room temperature. The breakthrough volume of EDME vapors was measured for various materials.

Many materials trapped EDME efficiently for example Silica gel (60–100 mesh 2 mm plug) charcoal, or quartz, glass or PYREX® wool or Teflon® treated with an acid which remains on the filter. Examples of such an acid include organic acids such as oxalic or citirc acid, or phosphoric acid. Most substrates capable of being coated with such an acid would be suitable for use as a filter material, however the material chosen was TEFLON® coated with citric acid for the following reasons:

citric acid coated TEFLON ® releases EDME efficiently when heated to 250° C.;
TEFLON ® can be shaped into a disk for easy insertion into a head for vacuum sampling;
the coated TEFLON ® filters can be prepared easily, at low cost;
citric acid is non-toxic (vs oxalic acid for example).

The vapor pressure was measured over a range of temperatures (−20° C. to +20° C.) according to a procedure published in (1). The pressure/temperature is given by the following equation:

$$\log P(ppb) = 16.54 - (3626/T(K)).$$

For example, at 25° C. the vapor pressure of EDME was calculated to be 23,6000 ppb.

Example 5
Analysis of Air Samples from Health and Welfare Canada Vault.

To determine the possibility of detecting cocaine and EDME vapors from seized cocaine samples, vapor samples were collected from the Health and Welfare Canada vault, where drug samples are stored as evidence in pending court cases. The probability of detecting cocaine and EDME vapors in this environment is high because large amount of drugs have been stored in the vault for long periods of time (months to years) and the air circulation in the vault is minimal. In addition, some drug paraphanelia, such as pipes for smoking crack, are also present in the vault.

A) Low Volume Sampling Pumps

For the analysis of air samples for cocaine, samples were collected with nine low volume sampling pumps (ca. 1 L/min), through glass tubing packed with silanized glass wool, for varying amounts of time as it was found to be a good adsorber for cocaine vapors. To avoid collecting particles of cocaine, the pumps were placed away from surfaces. The collected samples were desorbed from the glass wool and the vapors were recondensed into the needle of a gas tight syringe, according to a previously described procedure [8]. The syringe was filled with a solvent plug, the needle placed on the syringe and the sample was injected into a GC-MS for quantitation. The GC-MS was set for the detection of cocaine only (no monitoring of EDME; parameters listed in Table 3).

Figure 9:
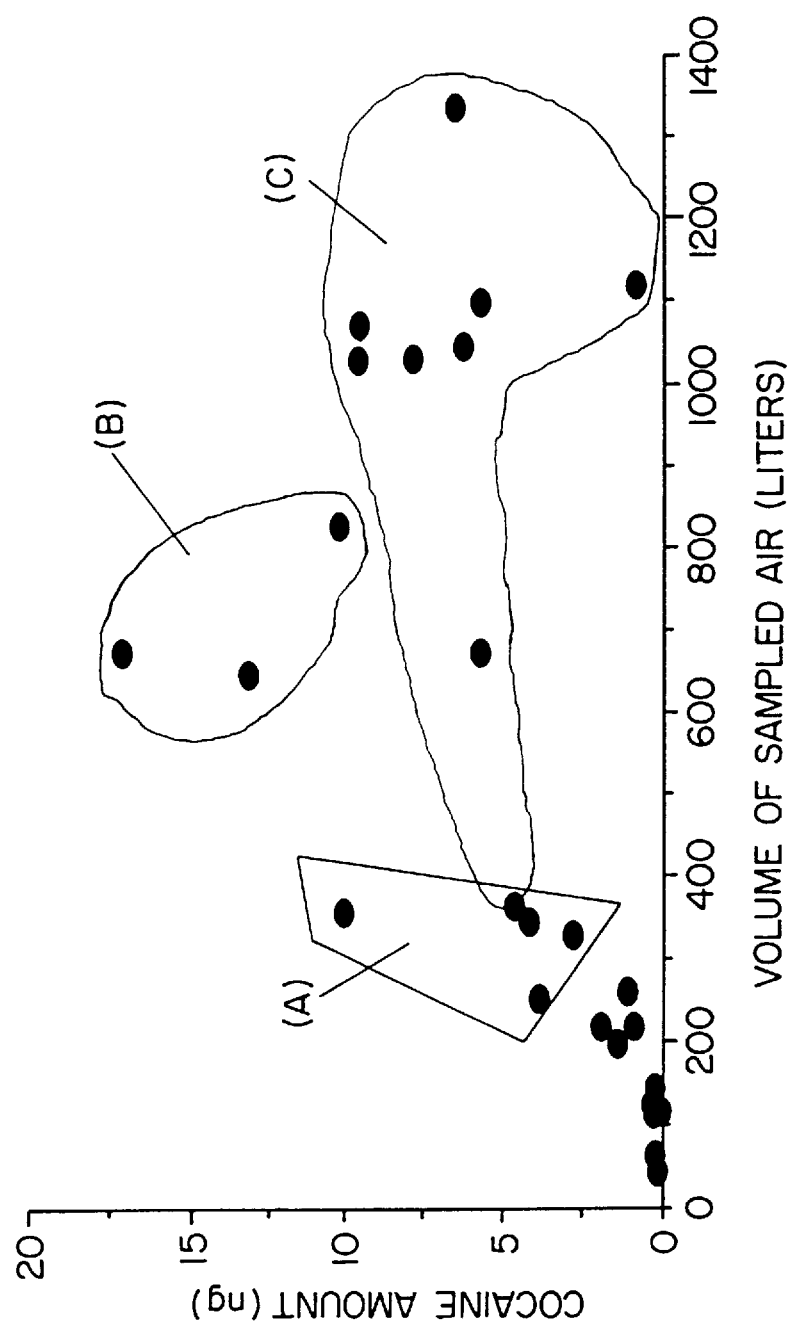
FIG. 9 shows the relationship between the amount of detectable cocaine and volume of air sampled over a 3 hour (A), 6 hour (B), or 8–12 hour period (C).

The results (FIG. 9) show a general increase in the amount of cocaine with volume sampled. All samples gave a positive result for cocaine. In addition, no abnormally high results, which would be indicative of the collection of large particles (ca. 100 $\mu$m), were observed.

B) High Volume Sampler.

Although the results with the small vacuum pump were promising, a high volume sampler may be required to increase the chances of trapping vapors from cargo containers and decreasing the sampling time, an operationally necessary parameter. This sampler must be powerful enough to allow a large flow of air through the filter assembly. The vacuum sampler chosen for our tests consisted of a vacuum pump which allowed an air flow of 250 L/min with the filter assembly.

Air samples were collected using the high volume sampler, with a filter holder with a short tube containing the filter holder assembly, but without a vacuum head. Three different configurations of filters were used to collect the air sample. They are shown below, with the filter listed in the order over which the air sample passed.

| Configuration #1 | Configuration #2 | Configuration #3 |
| --- | --- | --- |
| Metal pre-filter | Metal pre-filter | Metal pre-filter |
| Cotton filter | Cotton filter | Coated TEFLON ® filter |
| Coated TEFLON ® filter | Regular TEFLON ® filter | Cotton filter |

The metal pre-filter is present to trap lint and large dust particles. The second filter is present to trap small particulate matter and to stop and prevent them from reaching the third filter. The different configurations of the cotton and TEFLON® a filters were tested for the trapping efficiency of EDME and cocaine.

The metal pre-filter was placed on top of a TEFLON® cartridge which held the cotton and TEFLON® filters in their proper configurations. The short piece of plastic pipe coming in contact with the sampled air before the filters was washed with methanol between each sampling.

The filter holder was held in place approximately 10 feet inside the door of the vault by a metal ring attached to a buret stand. The air inlet into the vacuum was approximately 2 feet above the floor of the vault with the inlet facing the ceiling of the vault. The inlet was approximately 4 feet away from the walls of the vault and approximately 6 feet away from the ceiling. The exhaust of the vacuum was directed outside the vault (approximately 18 feet of hose).

For all samples collected, the metal pre-filter and the cotton filter were analyzed by IMS (operating parameters, Table 1) while the coated TEFLON® filter was analyzed by gas chromatography-mass spectrometry (GC-MS-MS, operating parameters, Table 4).

Transport blanks were collected to determine the effect of the storage material and the transportation on the filters used to collect the samples. The transport blank filters were taken out of their respective containers and placed in brown coin envelopes, in the same manner as all samples.

Spiked samples were prepared to determine the effect of time, storage material 5 and transportation on EDME and cocaine trapped on the different kinds of filters. 2 ng each of cocaine and EDME (2 $\mu$L of 1 ng/uL of each solution in methanol) were added to the filters. The solvent was left to evaporate and the filters were placed in brown coin envelopes.

Sampling site blanks were prepared to determine the background signals expected from filters placed inside the vault. The sampling site blanks were placed right below the sampling head, on a paper towel placed on the floor of the vault. The cotton wipes were placed on paper towels on the floor to the left and the right of the sampling assembly, on a filing cabinet to the right of the sampler and on a shelf to the left of the sampler. The sampling site blanks and the cotton swipes were placed at different time intervals in their proper position.

For the GC-MS analyses, a circle corresponding to the area where the air passed through the cotton filter and coated Teflon®filters was cut and introduced into a 0.25 inch O.D. diameter glass tube pinched into a rectangular opening at one end. Placed next to the filter were pieces of soda lime (total length of pieces is ca 1 cm). The filter/soda lime assembly was held in place by a plug of silanized glass wool. Dry nitrogen was flushed through the tube at 30 cc/min over the regular or coated TEFLON, soda lime and glass wool and the tube was heated to 250° C. for two minutes by means of a heated aluminum block. At the pinched end of the tube but physically outside the tube, a SPME (solid phase microextraction) needle was used to trap materials desorbed from the TEFLON®filter. The needle was then used to inject the adsorbed material into the GC-MS. Spiked samples with 1 ng of EDME and 1 ng of cocaine were also prepared and desorbed in the same manner as the samples from the vault, as control tests. In all cases, peaks were observed for cocaine and EDME. The alkaline medium, soda lime, prevents citric acid and other unwanted acid impurities from being detected.

The list of collected samples is shown in Table 6, including a detailed description of the sampling methodology. The filter type for each sample is listed from top to bottom in the order in which the sampled air encountered the filters.

TABLE 6

List of Collected Sample

| Sample # | Description | Sub Sample # | Filter Type |
| --- | --- | --- | --- |
| — | Transport blanks. Filters placed in envelope upon arrival at Health and Welfare Canada. | a | metal |
| | | b | cotton |
| | | c | coated TEFLON |
| | | d | regular TEFLON |
| — | Spiked samples. Filters spiked with 2 ng of EDME and 2 ng of cocaine. The filters were then placed in a brown envelope. | a | metal |
| | | b | cotton |
| | | c | coated TEFLON |
| | | d | regular TEFLON |
| — | Sampling site blanks. These filters were placed below the vacuum head on a paper towel on the floor of the vault while collection our first 15 minute | a | metal |
| | | b | cotton |
| | | c | coated TEFLON |

TABLE 6-continued

List of Collected Sample

| Sample # | Description | Sub Sample # | Filter Type |
|---|---|---|---|
| | sample (sample 7). | | |
| 1 | Filters placed in vacuum head for the 1st 5 minute sampling. These included a metal filter, followed by a cotton filter, followed by a coated TEFLON filter. | a b c | metal cotton coated TEFLON |
| 2 | Filters placed in vacuum head for the 1st 10 minute sampling. These included a metal filter, followed by a cotton filter, followed by a coated TEFLON filter. | a b c | metal cotton coated TEFLON |
| 3 | Filters placed in vacuum head for the 1st 15 minute sampling. These included a metal filter, followed by a cotton filter, followed by a coated TEFLON filter. | a b c | metal cotton coated TEFLON |
| — | Cotton swipes were placed in four positions in the vault during the first 15 minute sampling (sample 3). Two positions were on the floor, to the right and left of the sampler. Two positions were on filing cabinets or shelves, to the right and left of the sampler. | a b c d | cotton cotton cotton cotton |
| 4 | Filters placed in vacuum head for the 2nd 15 minute sampling. These included a metal filter, followed by a cotton filter, followed by a coated TEFLON filter. | a b c | metal cotton coated TEFLON |
| — | Sampling site blanks. These filters were placed below the vacuum head on a paper towel on the floor of the vault while collection our second 15 minute sample (sample 4). | a b c | metal cotton coated TEFLON |
| — | Cotton swipes were placed in four positions in the vault during the second 15 minute sampling (sample 4). Two positions were on the floor, to the right and left of the sampler. Two positions were on filing cabinets or shelves, to the right and left of the sampler. | a b c d | cotton cotton cotton cotton |
| 5 | Filters placed in vacuum head for the 2nd 10 minute sampling. These included a metal filter, followed by a cotton filter, followed by a coated TEFLON filter. | a b c | metal cotton coated TEFLON |
| 6 | Filters placed in vacuum head for the 2nd 5 minute sampling. These included a metal filter, followed by a cotton filter, followed by a coated TEFLON filter. | a b c | metal cotton coated TEFLON |
| 7 | Filters placed in vacuum head for the 3rd 15 minute sampling. These included a metal filter, followed by a cotton filter, followed by a coated TEFLON filter. | a b c | metal cotton coated TEFLON |
| 8 | Filters placed in vacuum head for the 1st 10 minute sampling. These included a metal filter, followed by a cotton filter, followed by a regular TEFLON filter. | a b c | metal cotton regular TEFLON |
| 9 | Filters placed in vacuum head for the 1st 15 minute sampling. These included a metal filter, followed by a cotton filter, followed by a regular TEFLON filter. | a b c | metal cotton regular TEFLON |
| — | Cotton swipes were placed in four positions in the vault during the collection of samples 6 to 9. Two positions were on the floor, to the right and left of the sampler. Two positions were on filing cabinets or shelves, to the right and left of the sampler. | a b c d | cotton cotton cotton cotton |
| 10 | Filters placed in vacuum head for the 1st 5 minute sampling. These included | a b | metal cotton |

TABLE 6-continued

List of Collected Sample

| Sample # | Description | Sub Sample # | Filter Type |
|---|---|---|---|
|  | a metal filter, followed by a cotton filter, followed by a regular TEFLON filter. | c | regular TEFLON |
| 11 | Filters placed in vacuum head for the 2nd 5 minute sampling. These included a metal filter, followed by a cotton filter, followed by a regular TEFLON filter. | a<br>b<br>c | metal<br>cotton<br>regular TEFLON |
| 12 | Filters placed in vacuum head for the 2nd 10 minute sampling. These included a metal filter, followed by a cotton filter, followed by a regular TEFLON filter. | a<br>b<br>c | metal<br>cotton<br>regular TEFLON |
| 13 | Filters placed in vacuum head for the 2nd 15 minute sampling. These included a metal filter, followed by a cotton filter, followed by a regular TEFLON filter. | a<br>b<br>c | metal<br>cotton<br>regular TEFLON |
| 14 | Filters placed in vacuum head for the 1st 15 minute sampling. These included a metal filter, followed by a coated TEFLON filter, followed by a cotton filter. | a<br>b<br>c | metal<br>coated TEFLON<br>cotton |
| 15 | Filters placed in vacuum head for the 1st 10 minute sampling. These included a metal filter, followed by a coated TEFLON filter, followed by a cotton filter. | a<br>b<br>c | metal<br>coated TEFLON<br>cotton |
| 16 | Filters placed in vacuum head for the 1st 5 minute sampling. These included a metal filter, followed by a coated TEFLON filter, followed by a cotton filter. | a<br>b<br>c | metal<br>coated TEFLON<br>cotton |
| 17 | Filters placed in vacuum head for the 2nd 5 minute sampling. These included a metal filter, followed by a coated TEFLON filter, followed by a cotton filter. | a<br>b<br>c | metal<br>coated TEFLON<br>cotton |
| 18 | Filters placed in vacuum head for the 2nd 10 minute sampling. These included a metal filter, followed by a coated TEFLON filter, followed by a cotton filter. | a<br>b<br>c | metal<br>coated TEFLON<br>cotton |
| 19 | Filters placed in vacuum head for the 2nd 15 minute sampling. These included a metal filter, followed by a coated TEFLON filter, followed by a cotton filter. | a<br>b<br>c | metal<br>coated TEFLON<br>cotton |
| — | Cotton swipes were placed in four positions in the vault during the collection of samples 10 to 19. Two positions were on the floor, to the right and left of the sampler. Two positions were on filing cabinets or shelves, to the right and left of the sampler. | a<br>b<br>c<br>d | cotton<br>cotton<br>cotton<br>cotton |

Analysis of Blank Filters and Spiked Filters.

The results of the analyses of various blank samples and spiked filters are shown in Table 7. The Ionscan analysis of metal and cotton filters used as transport blanks did not give alarms for cocaine or EDME.

TABLE 7

Analysis of Various Blanks and Spiked Filters

| Sample # | Description | Filter Type | IMS Results | GC-MS-MS Results |
|---|---|---|---|---|
| — | Transport Blank | Metal | Cocaine, Neg<br>EDME, Neg | — |
| — | Transport Blank | Cotton | Cocaine, Neg<br>EDME, Neg | — |
| — | Transport Blank | Regular TEFLON | — | — |
| — | Transport Blank | Coated TEFLON | — | Cocaine, Neg<br>EDME, Neg. |
| — | Spiked Sample, 2 ng cocaine, 2 ng EDME | Metal | Cocaine, 4132<br>EDME, 1448 | — |
| — | Spiked Sample, 2 ng cocaine, 2 ng EDME | Cotton | Cocaine, 198<br>EDME, Neg | — |
|  | Spiked Sample, | Coated | — | Cocaine, 22663 |

TABLE 7-continued

Analysis of Various Blanks and Spiked Filters

| Sample # | Description | Filter Type | IMS Results | GC-MS-MS Results |
|---|---|---|---|---|
| | 2 ng cocaine, 2 ng EDME | TEFLON | — | EDME, 10567 |
| | Spiked Sample, 2 ng cocaine, 2 ng EDME | Regular TEFLON | — | Cocaine, Neg EDME, Neg |

The spiked metal filter was analyzed less than 24 hours after the deposition of cocaine and EDME on the filter. Both cocaine and EDME were observed. The cotton filter was analyzed approximately 48 hours after the deposition of cocaine and EDME on the filter. Although cocaine was still present, EDME was not observed, again demonstrating that this compound is more volatile than cocaine. The GC-MS analysis of spiked samples was performed 72 to 96 hours after the deposition of the cocaine and EDME onto the filters. The results indicate that both cocaine and EDME remained on the coated teflon filter but EDME did not remain on the regular TEFLON filter.

Analysis of Filters in Configuration 1 (Metal, Cotton and Coated TEFLON®)

Table 8 shows the results obtained from air sampling of the vault through a metal filter, a cotton filter and a coated TEFLON® filter. For all filters, in all cases, cocaine was observed. No EDME was observed on metal pre-filters or cotton filters, indicating that the material does not get trapped as readily as cocaine or that it is not well retained, if trapped originally.

EDME and cocaine were observed on all coated TEFLON® filters analyzed by GC-MS. The sampling site filters and the cotton filters deposited in the vault during some of the sampling did not show any traces of cocaine, indicating that the presence of cocaine and EDME is not due to the presence of particulate matter in the air.

TABLE 8

Analysis of Filters in Holder Containing Metal, Cotton and Coated TEFLON.

| Sample # | Description | Filter Type | IMS Results | GC-MS-MS Results |
|---|---|---|---|---|
| 1 | 1st time, 5 minute sampling | Metal | Cocaine, 765 EDME, Neg | — — |
| | 1st time, 5 minute sampling | Cotton | Cocaine, 2002 EDME, Neg | — — |
| | 1st time, 5 minute sampling | Coated TEFLON | — — | Cocaine, 26890 EDME, 2162 |
| 2 | 1st time, 10 minute sampling | Metal | Cocaine, 1537 EDME, Neg | — — |
| | 1st time, 10 minute sampling | Cotton | Cocaine, 1644 EDME, Neg | — — |
| | 1st time, 10 minute sampling | Coated TEFLON | — — | Cocaine, 51542 EDME, 16531 |
| 3 | 1st time, 15 minute sampling | Metal | Cocaine, 2118 EDME, Neg | — — |
| | 1st time, 15 minute sampling | Cotton | Cocaine, 4072 EDME, Neg | — — |
| | 1st time, 15 minute sampling | Coated TEFLON | — — | Cocaine, 28633 EDME, 26658 |
| 4 | 2nd time, 15 minute sampling | Metal | Cocaine, 4052 EDME, Neg | — — |

TABLE 8-continued

Analysis of Filters in Holder Containing Metal, Cotton and Coated TEFLON.

| Sample # | Description | Filter Type | IMS Results | GC-MS-MS Results |
|---|---|---|---|---|
| | 2nd time, 15 minute sampling | Cotton | Cocaine, 8691 EDME, Neg | — — |
| | 2nd time, 15 minute sampling | Coated TEFLON | — — | Cocaine, 357974 EDME, 32948 |
| 5 | 2nd time, 10 minute sampling | Metal | Cocaine, 1449 EDME, Neg | — — |
| | 2nd time, 10 minute sampling | Cotton | Cocaine, 5090 EDME, Neg | — — |
| | 2nd time, 10 minute sampling | Coated TEFLON | — — | Cocaine, 4666 EDME, 268 |
| 6 | 2nd time, 5 minute sampling | Metal | Cocaine, 522 EDME, Neg | — — |
| | 2nd time, 5 minute sampling | Cotton | Cocaine, 2961 EDME, Neg | — — |
| | 2nd time, 5 minute sampling | Coated TEFLON | — — | Cocaine, 23130 EDME, 3255 |
| 7 | 3rd time, 15 minute sampling | Metal | Cocaine, 1519 EDME, Neg | — — |
| | 3rd time, 15 minute sampling | Cotton | Cocaine, 2401 EDME, Neg | — — |
| | 3rd time, 15 minute sampling | Coated TEFLON | — — | Cocaine, 36691 EDME, 3844 |

Sampling site blank filters left during the collection of samples 3 and 4 gave no alarm on IMS for the metal and cotton filters.

Analysis of Filters in Configuration 2 (Metal, Cotton and Regular TEFLON®)

Table 9 shows the results obtained when air from the vault was sampled through a metal pre-filter, a cotton and a regular TEFLON® filter. As in the previous experiment, the analysis of all three filters by IMS produced a cocaine alarm. No EDME peak was observed on any of the three filters. The GC-MS analysis indicated the presence of cocaine on one of the two 10 minute sampling and on both 15 minute sampling periods.

From Table 7, it is observed that no cocaine or EDME was detected on spiked regular TEFLON by GC-MS. This indicates that the GC-MS method is not as sensitive as IMS for cocaine deposited on regular TEFLON. Also, regular Teflon may not hold the EDME tightly enough to keep it on a filter for a sufficiently long time (i.e., days).

TABLE 9

Analysis of Filters in Holder Containing Metal, Cotton and Regular TEFLON

| Sample # | Description | Filter Type | IMS Results | GC-MS-MS Results |
|---|---|---|---|---|
| 8 | 1st time, 10 minute sampling | Metal | Cocaine, 545 EDME, Neg | — — |
| | 1st time, 10 minute sampling | Cotton | Cocaine, 2372 EDME, Neg | — — |
| | 1st time, 10 minute sampling | Regular TEFLON | Cocaine, 1746 EDME, Neg | Cocaine, Neg EDME, Neg |
| 9 | 1st time, 15 minute sampling | Metal | Cocaine, 546 EDME, Neg | — — |
| | 1st time, 15 minute sampling | Cotton | Cocaine, 3797 EDME, Neg | — — |
| | 1st time, 15 minute sampling | Regular TEFLON | Cocaine, 4269 EDME, Neg | Cocaine, 796 EDME, Neg |
| 10 | 1st time, 5 | Metal | Cocaine, 549 | — |

TABLE 9-continued

Analysis of Filters in Holder Containing Metal, Cotton and Regular TEFLON

| Sample # | Description | Filter Type | IMS Results | GC-MS-MS Results |
|---|---|---|---|---|
| | minute sampling | | EDME, Neg | — |
| | 1st time, 5 minute sampling | Cotton | Cocaine, 3497 EDME, Neg | — — |
| | 1st time, 5 minute sampling | Regular TEFLON | Cocaine, 2660 EDME, Neg | Cocaine, Neg EDME, Neg |
| 11 | 2nd time, 5 minute sampling | Metal | Cocaine, 558 EDME, Neg | — — |
| | 2nd time, 5 minute sampling | Cotton | Cocaine, 1583 EDME, Neg | — — |
| | 2nd time, 5 minute sampling | Regular TEFLON | Cocaine, 1772 EDME, Neg | Cocaine, Neg EDME, Neg |
| 12 | 2nd time, 10 minute sampling | Metal | Cocaine, 1397 EDME, Neg | — — |
| | 2nd time, 10 minute sampling | Cotton | Cocaine, 2611 EDME, Neg | — — |
| | 2nd time, 10 minute sampling | Regular TEFLON | Cocaine, 4202 EDME, Neg | Cocaine, 449 EDME, Neg |
| 13 | 2nd time, 15 minute sampling | Metal | Cocaine, 1872 EDME, Neg | — — |
| | 2nd time, 15 minute sampling | Cotton | Cocaine, 3158 EDME, Neg | — — |
| | 2nd time, 15 minute sampling | Regular TEFLON | Cocaine, 3487 EDME, Neg | Cocaine, 1380 EDME, 400 |

Analysis of Filters in Configuration 3 (Metal, Coated TEFLON® and Cotton)

Table 10 shows the results of the vault air sampling through a metal pre-filter, coated TEFLON® filter and cotton filter configuration. Cocaine was observed on all filters analyzed either by IMS or by GC-MS. EDME was only identified on coated Teflon analyzed by GC-MS.

The results outlined above indicate that cocaine was partially trapped on all three filters, regardless of the order in which these filters were placed and whether a regular or a coated TEFLON® filter was used. EDME was trapped and/or retained most efficiently on the coated TEFLON® filter.

In the metal—coated TEFLON®—cotton configuration, cocaine vapors broke through the middle coated TEFLON® filter onto the cotton filter while EDME vapors did not. This result is somewhat surprising since cocaine appears to adsorb more readily than EDME on many surfaces. This result may alternatively be explained by a breakthrough of both cocaine and EDME with EDME not being trapped and/or retained on the cotton filter. Similar results were obtained from filters used to collect air samples from a contaminated container in Miami (see below).

To maximize the chances of trapping cocaine and EDME vapors from containers, the following filter configuration is preferred: metal pre-filter, cotton and coated TEFLON®. The cotton in the middle position was found to give strong cocaine signals while the coated TEFLON® gave positive results for both cocaine and EDME.

TABLE 10

Analysis of Filters in Holder Containing Metal, Coated TEFLON and Cotton

| Sample # | Description | Filter Type | IMS Results | GC-MS-MS Results |
|---|---|---|---|---|
| 14 | 1st time, 15 minute sampling | Metal | Cocaine, 857 EDME, Neg | — — |
| | 1st time, 15 minute sampling | Coated TEFLON | — — | Cocaine, 12411 EDME, 9863 |
| | 1st time, 15 minute sampling | Cotton | Cocaine, 902 EDME, Neg | — — |
| 15 | 1st time, 10 minute sampling | Metal | Cocaine, 629 EDME, Neg | — — |
| | 1st time, 10 minute sampling | Coated TEFLON | — — | Cocaine, 55637 EDME, 10643 |
| | 1st time, 10 minute sampling | Cotton | Cocaine, 750 EDME, Neg | — — |
| 16 | 1st time, 5 minute sampling | Metal | Cocaine, 850 EDME, Neg | — — |
| | 1st time, 5 minute sampling | Coated TEFLON | — — | Cocaine, 1752 EDME, 1907 |
| | 1st time, 5 minute sampling | Cotton | Cocaine, 346 EDME, Neg | — — |
| 17 | 2nd time, 5 minute sampling | Metal | Cocaine, 819 EDME, Neg | — — |
| | 2nd time, 5 minute sampling | Coated TEFLON | — — | Cocaine, 815 EDME, 430 |
| | 2nd time, 5 minute sampling | Cotton | Cocaine, 550 EDME, Neg | — — |
| 18 | 2nd time, 10 minute sampling | Metal | Cocaine, 533 EDME, Neg | — — |
| | 2nd time, 10 minute sampling | Coated TEFLON | — — | Cocaine, 60454 EDME, 2815 |
| | 2nd time, 10 minute sampling | Cotton | Cocaine, 777 EDME, Neg | — — |
| 19 | 2nd time, 15 minute sampling | Metal | Cocaine, 927 EDME, Neg | — — |
| | 2nd time, 15 minute sampling | Coated TEFLON | — — | Cocaine, 85823 EDME, 3564 |
| | 2nd time, 15 minute sampling | Cotton | Cocaine, 1085 EDME, Neg | — — |

Example 6

Miami Container Study.

The high volume sampler was taken to Miami as part of field tests with marine cargo containers at the port of Miami and at Fort Lauderdale, between Feb. 19 and 23, 1996. The purpose of the tests was to determine whether high volume sampling is a viable method for the detection of drug vapors (cocaine and EDME) in marine containers. Some equipment details are summarized in Table 11.

The high volume sampler was described in Example 5. In this part of the study, the filters were attached to a vacuum head. The suction pump was powered by a portable power generator.

Sampling nozzles, made of plastic, were used to connect the filter assembly to the vents on the side of containers, allowing to sample the inside air. Typical sampling times were about 15 minutes. Several 45 foot containers were also tested which did not have any vents. In those containers, holes were drilled on the walls to allow the withdrawal of inside air. Sampling nozzles were attached to the container walls using duct tape and magnets.

The exposed TEFLON® filters were stored in marked envelopes and analyzed at a later date by GC/MS (operating parameters, Table 4) and IMS (operating parameters, Table 1). The results are presented in Table 12.

TABLE 11

Summary of Experimental Conditions During Air Sampling of Cargo Containers

| Sample # | Container # | Size[1] (feet) | Contents | Location | Conditions before/after Air Sampling | Sampling Time[2] (min) Plast. N | Metal. N |
|---|---|---|---|---|---|---|---|
| 1 | TPHU461832 | 40 | ? | Common yard | Not opened before/not destuffed | 15 | |
| 2 | SMLU720101 | 20 | ? | Guarded yard | Opened before/not destuffed | 15 | |
| 3 | MLCU243276 | 20 | ? | Guarded yard | Opened before/not destuffed | 20 | |
| 4 | KKLZ113121 | 45 | ? | Guarded yard | Opened before/not destuffed; sampling holes drilled in the wall | 15 | |
| 5 | APMU260669 | 20 | asphalt | Customs shed E | Not opened before/destuffed after | 15 | 15 |
| 6 | MAEU295578 | 20 | asphalt | Customs shed E | Not opened before/destuffed after | 20 | 15 |
| 7 | ICSU503947 | 20 | asphalt | Customs shed E | Opened before/not destuffed | 15 | |
| 8 | MAEU767388 | 20 | asphalt | Customs shed E | Opened before/not destuffed | 15 | 15 |
| 9 | REDZ231159 | 45 | aluminium wheels | Customs shed E | Not opened before/destuffed sampling holes drilled in the wall | 20 | |
| 10 | TRIU299977 | 20 | abrasives | Customs shed E | Not opened before/not destuffed | 15 | 15 |
| 11 | TEXU312686 | 20 | sewing machines | Ship side | Opened before/not destuffed | 15 | 15 |
| 12 | SMLZ760111 | 45 | textiles | Ship side | Not opened before/not destuffed sampling holes drilled in the wall | 15 | |
| 13 | TPHU689994 | 20 | ? | Ship side | Not opened before/not destuffed | 15 | 25 |
| 14 | ICSU481480 | 20 | ? | Ship side | Not opened/not destuffed (wipe sampling only) | | |
| 15 | TRIU299977 | 20 | abrasives | Customs shed E | Not opened before/destuffed after | 15 | 15 |
| 16 | TEXU343368 | 20 | ? | Customs shed E | Not opened before/destuffed after | 15 | 15 |
| 17 | TEXU279693 | 20 | ? | Customs shed E | Not opened before/destuffed after | 15 | 15 |
| 18 | TPHU605538 | 20 | ? | Customs shed E | Not opened before/destuffed after | 15 | 15 |
| 19 | CRXU290891 | 20 | ? | Customs shed E | Not opened before/destuffed after | | 15 |
| 20 | TRIU232392 | 20 | coffee beans | Ship side | Not opened before/not destuffed | | 15 |
| 21 | TRLU252681 | 20 | coffee beans | Ship side | Not opened before/not destuffed | | 15 |
| 22 | CRXU227807 | 20 | coffee beans | Ship side | Not opened before/not destuffed | | 15 |
| 23 | TPHU620827 | 20 | coffee beans | Ship side | Not opened before/not destuffed | | 15 |
| 24 | MLCU295617 | 20 | coffee beans | Ship side | Not opened before/not destuffed | | 15 |
| 25 | SMLU720035 | 20 | candy & lollipops | Ship side | Not opened before/destuffed after | | 15 |
| 26 | TPHU830545 | 20 | furniture (sofas) | Broward County Sheriff facility | Opened & destuffed before | 30 | 30 |

Notes:
[1] All 45 feet containers were aluminium trailers with no vents; holes were drilled into the walls of these containers and used for air sampling.
[2] The first sampling time refers to vapour sampling using a Plastic Nozzle, the second time to vapour sampling using a Metallic Nozzle/Gerry Bag.

TABLE 12

Results of Container Sampling for Drug Vapours

High Volume Air Sampling[1]

| Sample No. | Container No. | Teflon Filter by GC/MS | Gerry-Bag by IMS |
|---|---|---|---|
| 1 | TPHU461832 | Neg | —[2] |
| 2 | SMLU720101 | Neg | — |
| 3 | MLCU243276 | Neg | — |
| 4 | KKLZ113121 | Neg | — |
| 5 | APMU260669 | Neg | Neg |
| 6 | MAEU295578 | Neg | Neg |
| 7 | ICSU503947 | Neg | — |
| 8 | MAEU767388 | Neg | Neg |
| 9 | REDZ231159 | COCAINE ! | — |
| 10 | TRIU299977 | Neg | Neg |
| 11 | TEXU312686 | Neg | Neg |
| 12 | SMLZ760111 | Neg | — |
| 13 | TPHU689994 | Neg | Neg |
| 14 | ICSU481480 | — | — |
| 15 | TRIU299977 | Neg | Neg |
| 16 | TEXU343368 | Neg | Neg |
| 17 | TEXU279693 | Neg | Neg |
| 18 | TPHU605538 | Neg | Neg |
| 19 | CRXU290891 | — | Neg |
| 20 | TRIU232392 | Neg | Neg |
| 21 | TRLU252681 | Neg | Neg |
| 22 | CRXU227807 | Neg | Neg |
| 23 | TPHU620827 | Neg | HEROIN (105)[3] |
| 24 | MLCU295617 | Neg | Neg |
| 25 | SMLU720035 | Neg | Neg |
| 26 | TPHU830545 | EDME & COCAINE ! | COCAINE (116) |

[1] All air samples were analyzed at LSSD. Neg by GC-MS analysis indicates the absence of COCAINE & EDME, and Neg by IMS analysis means the absence of COCAINE, HEROIN, and EDME.
[2] Symbol "—" indicates that no sampling was performed.
[3] The number after the drug name indicates the amplitude of IMS signal as measured by Ionscan 400.

In addition to the system above, air sampling was also carried out using a different sampling nozzle made of metal which allowed the insertion of a treated Teflon® filter followed by a Gerry bag. The sampling head contained the filters and was attached to the vent of the container with duct tape. The metallic nozzle allowed air flows of approximately 500 L/min. The sampling time was approximately 15 minutes. The exposed Gerry Bags were stored in paper envelopes and analyzed off site for cocaine and associated compounds using IMS (Ionscan 400).

Air sampling was performed on an empty container from Columbia which was previously seized and which contained 35 kg of cocaine hydrochloride smuggled inside furniture. The container (#26) was left at the Broward County Sheriff facility in Fort Lauderdale, empty, for four days. The transit time from Columbia to Fort Lauderdale was another four days. No information was available as to the total residence time of the cargo inside this container. The empty container was kept in an open, unsheltered parking lot exposed to direct sunshine. This container was air-sampled twice for 30 minutes. The sampling was carried out in the middle of a sunny day, and the walls of the container and the extracted air were quite warm during the sampling.

Based on the results of the detailed examination of the cargo, none of the containers which were de-stuffed, with the exception of container #26, contained any drugs. As observed in Table 12, the presence of EDME vapors was uniquely associated with container #26. Container #26 also produced a strong signal for cocaine on a treated Teflon® filter indicating that vapors of cocaine were also present in the air. In addition, a Gerry bag placed after the Teflon® filter gave a positive signal for cocaine, indicating a breakthrough of cocaine vapors through the treated TEFLON® filter. This result is similar to those obtained at the HWC vault (see Example 5).

A positive signal for cocaine by GC-MS was also obtained for container #9. Since the subsequent manual search of the container yielded no drug seizure, the container may have been contaminated with cocaine from a previous shipment.

The results of the field tests at the Port of Miami indicated that high volume air sampling shows promise as a useful tool when searching cargo containers for hidden cocaine.

The present invention has been described with regard to preferred embodiments. However, it will be obvious to persons skilled in the art that a number of variations and modifications can be made without departing from the scope of the invention as described in the following claims.

References

[1] A. H. Lawrence, L. Elias, M. Authier-Martin, "Determination of Amphetamine, Cocaine, and Heroin Vapour Pressures Using a Dynamic Gas Blending System and Gas Chromatographic Analysis", Canadian Journal of Chemistry, Vol 62, No. 10 (1984) pp. 1886–1888.

[2] S. Browne, C. Bothe, D. Landstrom, "Trace Chemical Vapors in Illicit Cocaine Production and Shipping", Cargo Inspection Technologies, SPIE Proceedings, Vol 2276, (1994) pp. 340–351.

[3] E. J. Poziomek, S. Chen, H. Wohltjen, N. L. Jarvis, "Use of chemical markers in designing detection and identification schemes for cocaine and cocaine hydrochloride", Contraband and Cargo Inspection Technology International Symposium, Proceedings, Washington, D.C., 1992, pp. 425–432.

[4] W. H. Robbins, B. W. Wright, "Analysis of Volatile Organic Compounds from Illicit Cocaine Samples", Cargo Inspection Technologies, SPIE Proceedings, Vol 2276 (1994) pp. 352–362.

[5] T. Lukaszewski, W. K. Jeffery, "Impurities and Artifacts of Illicit Cocaine", J. Forensic Sciences, Vol 25, No. 3 (1980) pp. 499–507.

[6] J. F. Casale, R. W. Waggoner, "A Chromatographic Impurity Signature Profile Analysis for Cocaine Using Capillary Gas Chromatography", J. Forensic Sciences, Vol 36, No. 5 (1991) pp. 1312–1330.

[7] F. G. Ensing, C. Racamy, R. A. de Zeeuw, "A Rapid Gas Chromatographic Method for the Fingerprinting of Illicit Cocaine Samples", J. Forensic Sciences, Vol 37, No. 2 (1992) pp. 446–459.

[8] A. H. Lawrence, "Simple Interface for Transferring High-Boiling Compounds from Sample Adsorption Tubes onto Capillary Gas Chromatographic Columns", J. Chromatography, Vol 395 (1987) pp. 531–538.

[9] L. H. Kim, L. L. Danyelewych-May, R. Jadamec, C. Su, S. Rigdon, L. Norwood, D. Hoglund, "Cargo Contraband Screening", Cargo Inspection Technol. Vol 2276 (1994) pp. 279–291.

The embodiments of the invention on which an exclusive property or privilege is claimed are defined as follows:

1. A method for the detection of cocaine, comprising obtaining a sample of air, passing the sample through a filter capable of retaining the vapors of cocaine and associated compounds, removing the compounds from the filter and detecting the presence of cocaine and associated compounds said associated compounds having a higher vapor pressure than that of cocaine, and said associated compounds containing the molecular bicyclic structure of cocaine.

2. The method of claim 1 wherein one of the associated compounds is ecgonidine methyl ester (EDME).

3. The method of claim 2 wherein vapors of the associated compounds dissipate from a contained space before the vapors of cocaine, such that the detection of EDME or the co-detection of the vapors of cocaine and EDME indicates the presence of cocaine in the contained space.

4. The method of claim 1 wherein the filter capable of retaining the vapors of cocaine and associated compounds is chosen from the group consisting of tissue, cloth, or mesh made from paper, cotton, silanized glass wool, metal, or TEFLON®.

5. The method of claim 4 wherein the filter has been treated with a surface activating material, which remains on the filter, to enhance the binding of vapors of cocaine and associated compounds.

6. The method of claim 5 wherein the surface activating material is comprised of an acidic material.

7. The method of claim 6 wherein the surface activating material is chosen from the group consisting of citric, oxalic, or phosphoric acid or other acid exhibiting similar normalities or pH.

8. The method of claim 7 wherein the surface activating material is citric acid.

9. The method of claim 1 wherein the method for the detection of the vapors of cocaine and associated chemicals involves ion mobility spectrometry (IMS), IMS-mass spectrometry (MS), gas-chromatography (GC), GC-MS, or GC-MS-MS.

10. The method of claim 6 wherein the acidic surface activating material is chosen from the group consisting of citric, oxalic, or phosphoric acid, or other acid exhibiting similar normalities or pH.

11. The method of claim 10 wherein the surface activating material is citric acid.

12. The method of claim 7 wherein the method of detection of the vapors of cocaine and associated compounds involves the release of cocaine and associated compounds from acid treated filters by heating in the presence of an alkaline medium, and detection of released compounds by ion mobility spectrometry (IMS), IMS-mass spectrometry (MS), gas-chromatography (GC), GC-MS, or GC-MS-MS.

13. The method of claim 12 wherein the alkaline medium is comprised of alkaline metal or alkaline earth metal oxides and hydroxides.

14. The method of claim 13 wherein the alkaline medium is comprised of soda lime.

15. A filter capable of binding vapors of ecgonidine methyl ester (EDME), chosen from the group consisting of tissue, cloth or mesh made from paper, cotton wool, metal, or TEFLON® and which has been treated with activating material which remains on the filter and enhances the binding of EDME.

16. A device for sampling air suspected of containing vapors of cocaine and associated compounds, comprising a nozzle made up of:
   a) a sampling component comprising an opening for drawing a sample of air, and
   b) a filtering component comprising a filtration device and vacuum port, such that the device is placed in the path of air obtained from the sampling component as it is withdrawn through the vacuum port, said filtration device comprised of a plurality of filters capable of removing particulates from the air and, at least one of which is capable of binding vapors of cocaine, and at least one filter comprising the filter of claim 13.

17. A device for sampling air suspected of containing vapors of cocaine and associated compounds, comprising a nozzle made up of:
   a) a sampling component comprising an opening for drawing a sample of air, and
   b) a filtering component comprising a filtration device and vacuum port, such that the filtration device is placed in the path of air obtained from the sampling component as it is withdrawn through the vacuum port, said filtration device comprised of at least two filters;
      i) the first filter capable of removing particulates and binding vapors of cocaine from the air, said first filter chosen from the group consisting of tissue, cloth, or mesh made from paper, cotton, silanized glass wool, metal, or TELFON®;
      ii) the second capable of binding vapors of cocaine and associated compounds, said second filter chosen from the group consisting of tissue, cloth, or mesh made from paper, cotton, metal, or TEFLON® which has been treated with a surface activating material chosen from the group consisting of citric, oxalic, or phosphoric acid or other acid exhibiting similar normalities or pH.

* * * * *